(12) United States Patent
Heiskell et al.

(10) Patent No.: US 10,209,140 B1
(45) Date of Patent: Feb. 19, 2019

(54) PORTABLE TEMPERATURE PROBE

(71) Applicants: Joshua Paul Heiskell, San Francisco, CA (US); Ronald Edmund Heiskell, Tracy, CA (US); Daniel Christopher Quigg, Tracey, CA (US)

(72) Inventors: Joshua Paul Heiskell, San Francisco, CA (US); Ronald Edmund Heiskell, Tracy, CA (US); Daniel Christopher Quigg, Tracey, CA (US)

( * ) Notice: Subject to any disclaimer, the term of this patent is extended or adjusted under 35 U.S.C. 154(b) by 190 days.

(21) Appl. No.: 15/404,257

(22) Filed: Jan. 12, 2017

Related U.S. Application Data

(60) Provisional application No. 62/269,787, filed on Dec. 18, 2015.

(51) Int. Cl.
| | |
|---|---|
| *G01K 13/00* | (2006.01) |
| *G01K 1/08* | (2006.01) |
| *G01K 1/16* | (2006.01) |
| *G01N 33/24* | (2006.01) |
| *G01N 3/40* | (2006.01) |

(52) U.S. Cl.
CPC ............. *G01K 13/00* (2013.01); *G01K 1/08* (2013.01); *G01K 1/16* (2013.01); *G01N 3/40* (2013.01); *G01N 33/24* (2013.01)

(58) Field of Classification Search
CPC .. G01K 1/00; G01K 1/08; G01K 1/16; G01K 13/00; G01N 3/40; G01N 33/02; G01N 33/18; G01N 33/24
USPC ............... 116/200, 205; 374/155; 73/81–85; 99/341, 342; D7/683; D10/57, 58
See application file for complete search history.

(56) References Cited

U.S. PATENT DOCUMENTS

| | | | | |
|---|---|---|---|---|
| 339,176 | A * | 4/1886 | Hempel | G01K 13/00 374/155 |
| 3,254,533 | A * | 6/1966 | Tongret | G01K 13/002 116/216 |
| 3,785,208 | A * | 1/1974 | Marsilia et al. | G01K 1/083 374/202 |
| 3,967,502 | A * | 7/1976 | Moran | G01K 1/14 374/31 |
| 4,052,890 | A * | 10/1977 | Kammlah et al. | G01N 3/42 73/81 |
| 4,260,261 | A * | 4/1981 | Mann et al. | G02B 23/2423 356/402 |
| 4,445,788 | A * | 5/1984 | Twersky et al. | G01K 1/026 374/142 |

(Continued)

FOREIGN PATENT DOCUMENTS

JP 2008164478 A * 7/2008 ............. G01N 33/24

*Primary Examiner* — R. A. Smith
(74) *Attorney, Agent, or Firm* — Law Office of Mark Levy

(57) ABSTRACT

A portable temperature probe. The probe has a handle probe assembly with a longitudinal, steel, antimicrobial, heat-conductive element. A removable, hollow, stainless steel sheath is provided for enclosing and protecting the probe assembly. The heat-conductive element is hardened to resist bending and silver plated for maximum heat-conductivity. The sheath can be carried in a pocket to keep the probe easily accessible, sanitary, and protected from bending. A magnetic closure on the sheath allows the probe to be quickly accessible for removal and storage. The entire unit can be sanitized along with other kitchen utensils without corroding.

17 Claims, 4 Drawing Sheets

(56) References Cited

U.S. PATENT DOCUMENTS

| | | | | |
|---|---|---|---|---|
| 4,457,633 | A | * | 7/1984 | Andrews .................. G01K 7/16 |
| | | | | 206/306 |
| D287,829 | S | * | 1/1987 | Osaka ............................ D10/57 |
| 4,642,785 | A | * | 2/1987 | Packard et al. ...... G01K 13/002 |
| | | | | 374/102 |
| D300,908 | S | * | 5/1989 | Chan .............................. D10/57 |
| 4,939,927 | A | * | 7/1990 | Johnston .................. G01N 3/42 |
| | | | | 426/231 |
| 6,676,004 | B1 | * | 1/2004 | Trapp et al. ....... B23K 20/1255 |
| | | | | 228/112.1 |
| 7,654,737 | B2 | * | 2/2010 | Chab et al. ............ G01K 1/146 |
| | | | | 206/306 |
| 2017/0254706 | A1 | * | 9/2017 | Ganrude et al. ....... G01N 33/02 |

\* cited by examiner

PORTABLE TEMPERATURE PROBE

RELATED PATENT APPLICATION

The present application is related to provisional patent application no. 62/269,787, for MEANS FOR DETERMINING THE INTERNAL DONENESS OF FOOD, filed Dec. 18, 2015, and hereby incorporates the teaching therein by reference. The priority date of the aforementioned application is hereby claimed.

FIELD OF THE INVENTION

The present invention relates to temperature probes and, more specifically, to a portable temperature probe for measuring the temperature of elements and the internal temperature of food being cooked.

BACKGROUND OF THE INVENTION

For years chefs and cooks alike have been faced with the dilemma of determining the doneness of food, which is the condition of being cooked to the desired degree. For example, the desired degree of cooked meat is rare, medium or well done. There are many factors affecting how quickly meat cooks, such as temperature, thickness, percentage of fat, and the presence or absence of bone. Similar internal variations can be found in all foods, so for these reasons time and temperature cooking charts are not accurate.

Due to this problem chefs have adopted other means to determine when to remove food from heat to acquire the desired doneness. Many times they will use a "cake tester" which consists of a thin metal rod with a small plastic molded finger grip. The chef inserts a cake tester into the food to feel the texture and then places the metal rod of the tester on his/her lip or other part of their body to check the temperature in relationship to their body temperature. As an example, if meat is pierced with a metal rod and the chef touches the rod to his lip and the rod is cooler than the chef's lip, he knows that the meat is rare. The cake tester, however, has shortcomings. The rod is made of a metal that conducts heat very slowly, the rod is often subject to bending, and there is no convenient place for chefs to place it in their jacket where it is sanitary and where they can easily and quickly acquire it, no matter where they are in the kitchen.

Cake testers are designed to test cakes, not other foods like steak, fish, potatoes, etc., so they are not constructed of a durable metal that conducts or transmits heat quickly; nor are they made to resist bending that might occur when inserting the probe into food. There is also no sanitary means for a chef to carry a cake tester or any other metal rod in a convenient place that protects it from contamination and prevents it from bending while being carried.

Cake testers or other metal rods or probes that a chef might use are constantly falling out of pockets and getting lost. They can be difficult to retrieve from a pocket. As mentioned, the metal used in all existing probes is a poor conductor of heat.

SUMMARY OF THE INVENTION

In accordance with the present invention, there is provided a portable temperature probe. The probe has a handle probe assembly with a longitudinal, steel, heat-conductive element. A removable, hollow, stainless steel sheath is provided for enclosing and protecting the probe assembly. The heat-conductive element is hardened to resist bending and silver plated for maximum heat-conductivity. The sheath can be carried in a pocket to keep the probe easily accessible, sanitary, and protected from bending. A magnetic closure on the sheath allows the probe to be quickly accessible for removal and storage. The entire unit can be sanitized along with other kitchen utensils without corroding.

BRIEF DESCRIPTION OF THE DRAWINGS

A complete understanding of the present invention may be obtained by reference to the accompanying drawings, when considered in conjunction with the subsequent detailed description, in which.

Like reference numerals refer to like parts throughout the several views of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

A portable temperature has a handle probe assembly with a longitudinal, steel, heat-conductive element that is silver plated. A removable, hollow, stainless steel sheath is provided for enclosing and protecting the handle probe assembly. A magnetic closure on the sheath allows the probe to be quickly accessible for removal and storage.

Figure 1:
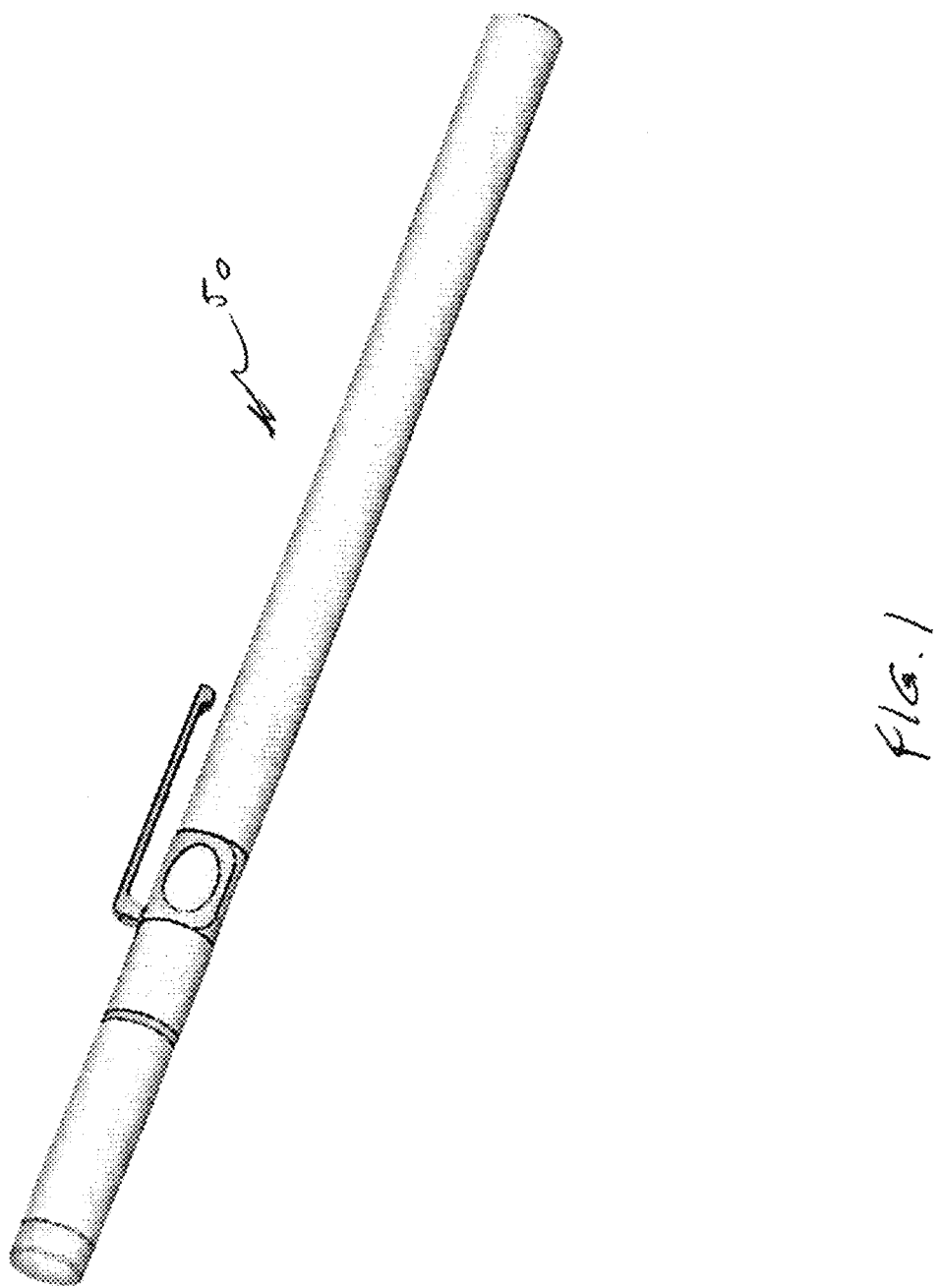
FIG. 1 is a perspective view of a portable temperature probe in accordance with the present invention.

Referring now to FIG. 1, there is shown a portable temperature probe 50 in accordance with the invention. The dimensions of probe 50 are commensurate with a writing pen, not shown, and can easily be inserted into a shirt or jacket pocket.

Figure 2:
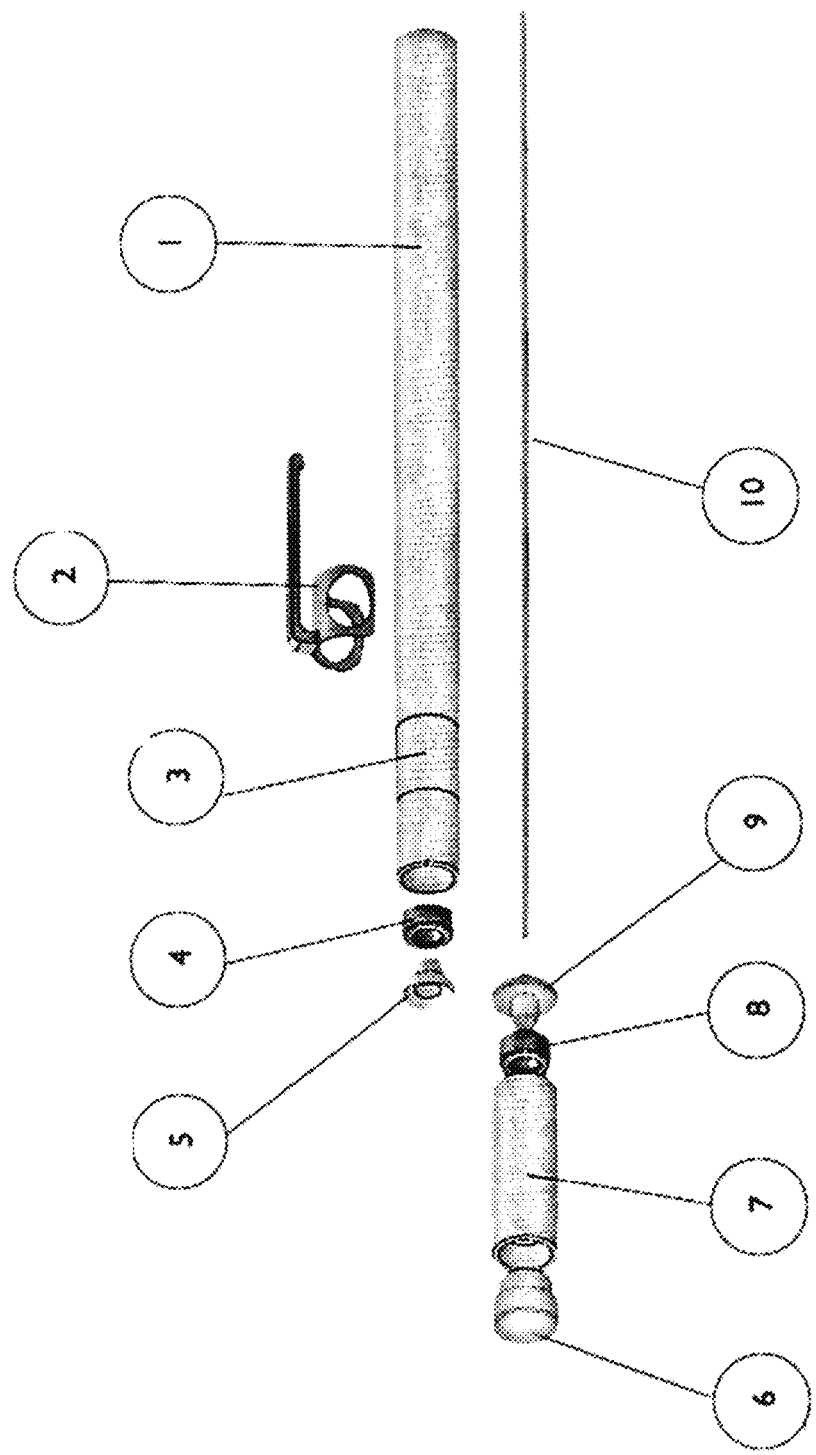
FIG. 2 is an exploded view of the portable temperature probe shown in FIG. 1.

Referring now also to FIG. 2, probe 50 is shown in exploded view. In the preferred embodiment, the elements of the inventive probe 50 include:

1. a sanitary sheath made of 316 stainless steel with a nominal OD of 0.3125";
2. a pocket clip of the band style, corrosion resistant, with sufficient gripping power to secure in an individual's pocket;
3. an annular area with an outside diameter of 0.297";
4. a neodymium rare earth magnet with a pull force of 1.53 foot pounds of force;
5. a plastic funnel having an annular decreasing inside diameter running from end to end while maintaining a minimum inside diameter of 0.046875";
6. a C145 tellurium copper end cap with an outside diameter of 0.3125";
7. a corrosion resistant probe handle made of 316 stainless steel, with an outside diameter of 0.3125";
8. a neodymium rare earth magnet with a pull force of 1.53 foot pounds of force;

9. a C145 tellurium copper insulator with an outside diameter of 0.3125"; and 10. a centerless ground H13 nitrided steel, silver-plated, antimicrobial probe with a core harness of 50-55 HRC.

While the aforementioned materials, properties, and dimensions have been found to be preferred, it should be understood that alternative materials and dimensions can be incorporated in the inventive portable temperature probe without departing from the scope of the invention.

A sheath 1 is of sufficient length to encircle a heat-conductive element 10 and protect it end to end from unsanitary contact and from bending. Sheath 1 also provides means to carry heat-conductive element 10 in a shirt or jacket pocket, not shown.

An annular ring 3 on sheath 1 receives a pocket clip 2 and prevents pocket clip 2 from sliding off of sheath 1. The band-style pocket clip 2 could be replaced with a screw-on, a circle ring style, or other style pocket clip, eliminating the need for the reduced diameter annular area on sheath 1.

A sheath magnet 4 is pressed into the inside diameter of sheath 1 and is attracted to a handle magnet 8 that is pressed into a handle 7 to magnetically grip handle 7 and sheath 1 together. Instead of using magnets to secure handle probe assembly 55 to sheath 1, other methods could be employed, such as male and female threads, a toggle closure mechanism, a clasp, a friction closure, non-threaded fasteners such as pins, keys or dowels, a bayonet connector employing a quarter, half, three-quarter, or full turn removal, press fit, an electricity-activated button/latch, a rubber grommet or an O-ring friction closure, a hook and loop fastener, a taper pin, a spring pin, also called a tension pin or roll pin, an eccentric grasp, an R-clip, also known as a spring cotter pin, a linchpin, a latch, a terry clip, or a lobster clasp.

A magnetic insulator 9 is pressed into handle magnet 8 to hold it securely into handle 7 to reduce the magnetic attraction of magnets 4 and 8, providing a sufficient amount of holding power between sheath 1 and handle 7.

Instead of press fitting heat-conductive element 10 into insulator 9 and end cap 6, insulator 9 could be a slip fit with a press fit occurring only at end cap 6 or vice-versa. The tight fit of element 10 into end cap 6 and/or insulator 9 could also be achieved by the use of male and female threads or other means of adherence such as brazing, welding or soldering.

Heat-conductive element 10 is securely fastened to handle 7 by a press fit into a copper insulator 9, as is well known in the art. In the preferred embodiment, heat-conductive element 10 is silver plated, hardened steel, but any other suitable, heat-conductive material can be used, including but not limited to, copper or gold. The silver coating is antimicrobial.

An end cap 6 is pressed into handle 7. A plastic funnel 5, which is pressed into sheath magnet 4, provides a guide to allow heat-conductive element 10 to be inserted into sheath 1. Sheath 1, handle 7, insulator 9, and end cap 6 could be constructed of other suitable materials such as plastic, wood, glass, fiberglass, other metals or a combination thereof.

Funnel 5 also provides a low friction contact point so that silver plating on heat-conductive element 10 will not be removed by repeated withdrawals and insertions out of and into sheath 1.

Sheath 1 is inserted into a pocket or other readily accessible location, not shown, and held in place by pocket clip 2. Probe handle 7 is held firmly in place by the magnetic attraction of sheath magnet 4 and handle magnet 8. Magnets 4 and 8 are preferably pressed into the inside diameters of the sheath tube 1 and the handle tube 7, respectively.

The strength of the magnetic attraction between handle 7 and sheath 1 is controlled by the dimensions of insulator 9, which is pressed into the inside diameter of handle magnet 8. The magnetic attraction between the sheath and the handle magnets 4 and 8 secures handle 7 onto sheath 1 until sufficient pull force is exerted on handle 7 to remove handle 7 from the sheath 1. Heat-conductive element 10 is attached to handle 7 by a pressed fit into end cap 6 and insulator 9.

In operation, when a user desires to test the cooking status of a food, he removes the handle/heat-conductive element 10 from sheath 1, which releases easily. After testing the food's cooking status, the user inserts handle/heat-conductive element 10 combination back into sheath 1 by placing the distal end of heat-conductive element 10 against funnel 5, which guides heat-conductive element 10, centering it into sheath 1. When handle magnet 8 is in close proximity to sheath magnet 4, handle 7 and sheath 1 snap closes. Sheath 1 protects heat-conductive element 10 from bending. Sheath 1 also keeps heat-conductive element 10 sanitary until its next use by shielding it from outside contaminates which may reside in the user's pocket. Because the aforementioned components resist corrosion, the entire unit 50 can be sanitized as needed.

Figure 3:
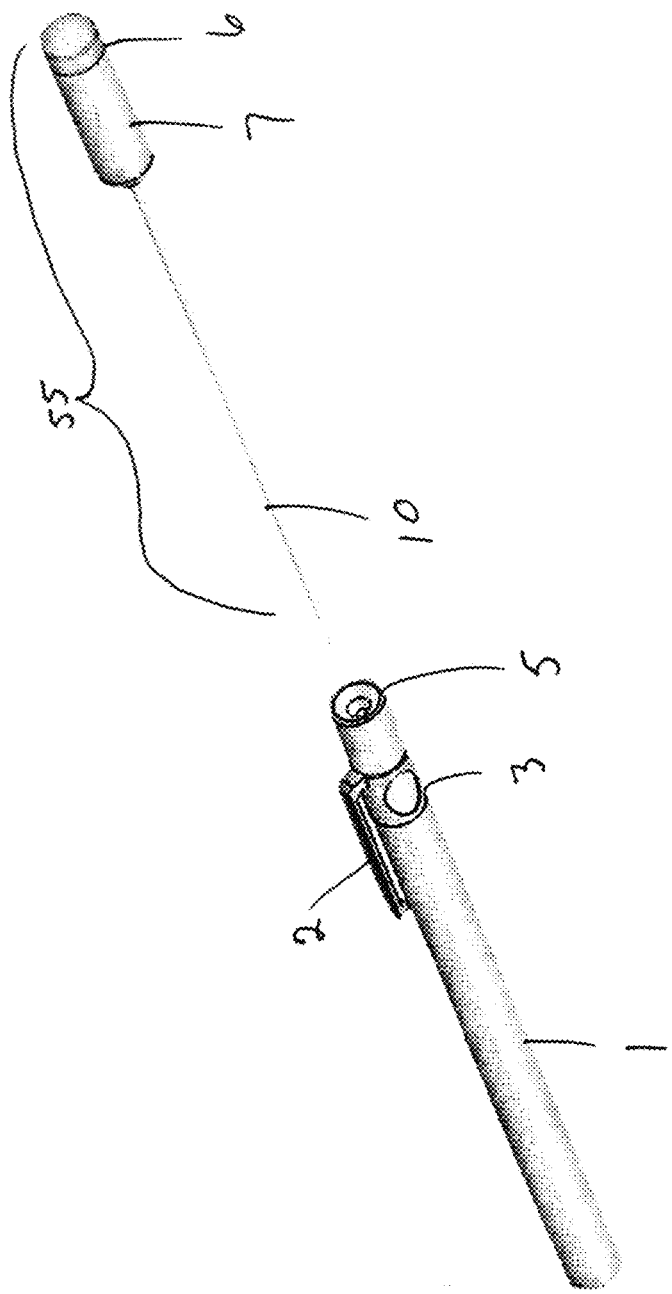
FIG. 3 is a perspective view of the portable temperature probe removed from its sheath.

Referring now also to FIG. 3, there is shown heat-conductive element 10, handle 7, and cap 6 (hereinafter the handle probe assembly 55) removed from sheath 1.

Figure 4:
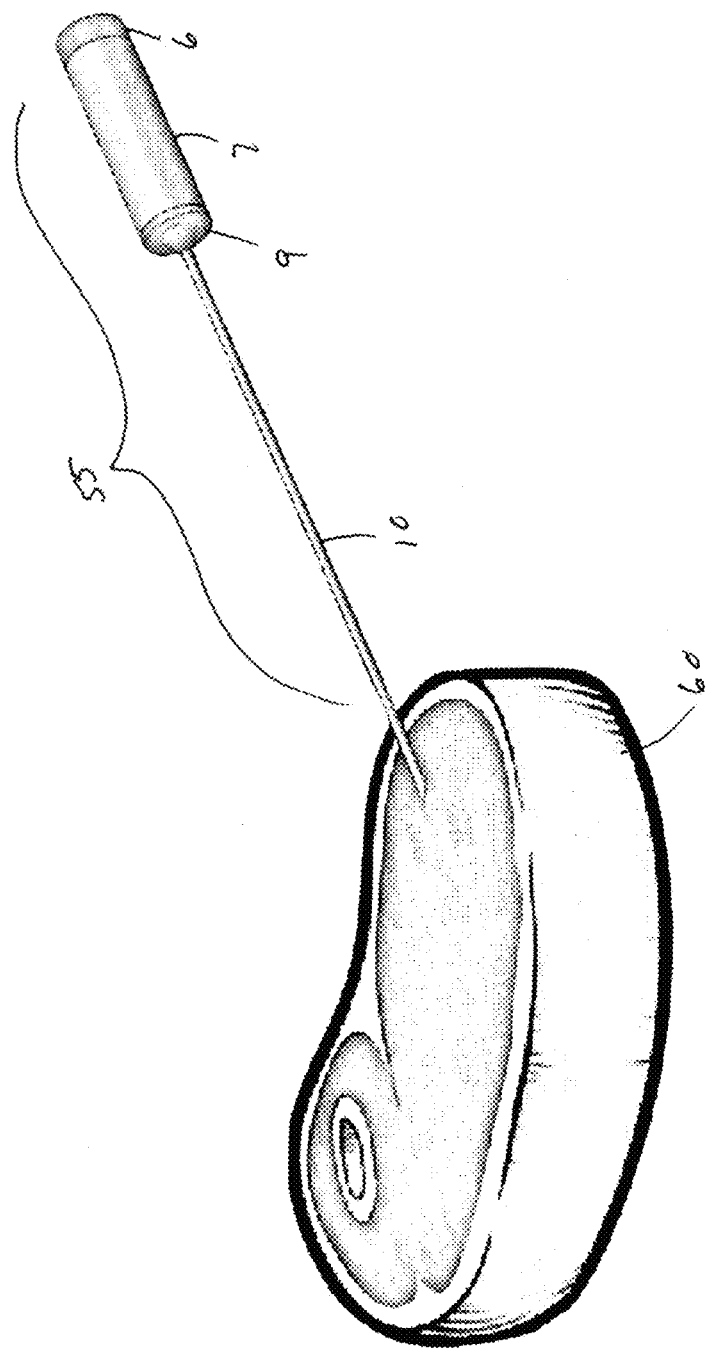
FIG. 4 is a perspective view of the portable temperature probe inserted into a steak.

Referring now to FIG. 4, there is shown handle probe assembly 55 inserted into a steak 60. As stated hereinabove, the user simply grasps handle 7 to remove handle probe assembly 55 from sheath 1, which is located in his/her pocket or other convenient location, secured by the pocket clip 2. The user then inserts handle probe assembly 55 into the food 60 (e.g., steak, fish, potato or baked goods). The piercing of food 60 allows the user to determine the texture thereof. Additionally, when the user then touches heat-conductive element 10 to a part of his/her body, such as a lip, the user is able to determine the relative temperature of food 60. By discovering the texture and/or the temperature of food 60, the user can determine the doneness, or the condition of being cooked to the desired degree.

This device 50 might also be useful in testing the hardness of topsoil, and the presence or absence of tree roots, without the need of disturbing the surface soil. It might also be useful in testing the depth of roofing materials without the need to take a core sample. It might also be useful in detecting bad bearings when handle probe assembly 55 is placed on a moving bearing and a person's ear is placed on the probe handle. It could also detect overheated moving machine parts, indicating a possible problem, that are difficult to isolate or access with conventional temperature sensing devices. It might also be used to pierce films to determine relative tensile strength.

The inventive device 50 may also be useful in testing the hardness of top soil, and the presence or absence of tree roots, without the need of disturbing the surface soil. It may also be useful in testing the depth of roofing materials without the need to take a core sample. It may also be useful in detecting bad bearings when probe 50 is placed on a moving bearing and a person's ear is placed on probe handle 7. It can also detect overheated moving machine parts, indicating a possible problem, which is usually difficult to isolate or access with normal temperature sensing devices. Probe 50 may also be used to pierce films to determine relative tensile strength.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A portable temperature probe comprising:
 a) a longitudinal heat-conductive element having a proximal end and a distal end;
 b) a magnetic insulator having a front surface and a rear surface, said front surface being operatively connected to said proximal end of said longitudinal heat-conductive element; and
 c) a handle operatively connected to said rear surface of said magnetic insulator, said longitudinal heat-conductive element, said magnetic insulator, and said handle forming a probe assembly.

2. The portable temperature probe in accordance with claim 1, further comprising a removable, hollow, longitudinal sheath having an outer surface, a proximal end, and a distal end for enclosing and protecting said longitudinal heat-conductive element, said distal end of said hollow, longitudinal sheath terminating in a solid surface.

3. The portable temperature probe in accordance with claim 2, wherein said hollow, longitudinal sheath further comprises a pocket clip attached to said outer surface thereof.

4. The portable temperature probe in accordance with claim 2, wherein said hollow, longitudinal sheath further comprises a tapered funnel for guiding said longitudinal heat-conductive element, said tapered funnel being proximate said distal end of said hollow, longitudinal sheath.

5. The portable temperature probe in accordance with claim 4, wherein said hollow, longitudinal sheath further comprises a first magnet disposed between said tapered funnel and said proximal end of said hollow, longitudinal sheath, and said probe assembly further comprises a second magnet disposed between said handle and said rear surface of said magnetic insulator.

6. The portable temperature probe in accordance with claim 5, wherein said first and said second magnets comprise neodymium rare earth magnets.

7. The portable temperature probe in accordance with claim 1, wherein said longitudinal heat-conductive element comprises silver-plated, centerless ground H13 nitrided steel, said silver plating being antimicrobial.

8. The portable temperature probe in accordance with claim 1, wherein said probe assembly further comprises an end cap operatively connected to said handle.

9. The portable temperature probe in accordance with claim 8, wherein said end cap comprises C145 tellurium copper.

10. The portable temperature probe in accordance with claim 1, wherein said handle comprises stainless steel.

11. A portable temperature probe, comprising:
 a) a probe assembly comprising a longitudinal heat-conductive element comprising silver-plated, centerless ground H13 nitrided steel, wherein the probe assembly comprises:
  a') a proximal end and a distal end;
  b') a magnetic insulator having a front surface and a rear surface, said front surface being operatively connected to said proximal end of said longitudinal heat-conductive element; and
  c') a handle operatively connected to said rear surface of said magnetic insulator; and
 b) a removable, hollow, longitudinal sheath having a proximal end and a distal end for enclosing and protecting the probe assembly.

12. The portable temperature probe in accordance with claim 11, wherein said hollow, longitudinal sheath comprises a tapered funnel for guiding said longitudinal heat-conductive element, said tapered funnel being proximate said distal end of said hollow, longitudinal sheath.

13. The portable temperature probe in accordance with claim 12, wherein said hollow, longitudinal sheath further comprises a first magnet disposed between said tapered funnel and said proximal end of said hollow, longitudinal sheath, and said probe assembly further comprises a second magnet disposed between said handle and said rear surface of said magnetic insulator.

14. The portable temperature probe in accordance with claim 13, wherein said first and said second magnets comprise neodymium rare earth magnets.

15. The portable temperature probe in accordance with claim 11, wherein said probe assembly further comprises an end cap operatively connected to said handle.

16. The portable temperature probe in accordance with claim 15, wherein said end cap comprises C145 tellurium copper.

17. The portable temperature probe in accordance with claim 11, wherein said handle comprises stainless steel.

* * * * *